United States Patent
Shitoto

[19]

[11] Patent Number: 5,876,403
[45] Date of Patent: Mar. 2, 1999

[54] BONE-FIXING DEVICES

[75] Inventor: Hideo Shitoto, Tokyo, Japan

[73] Assignee: Robert Reid Inc., Tokyo, Japan

[21] Appl. No.: 923,294

[22] Filed: Sep. 4, 1997

[30] Foreign Application Priority Data

Sep. 9, 1996 [JP] Japan ................................. 8-257539

[51] Int. Cl.⁶ .................................................. A61B 17/56
[52] U.S. Cl. ................................ 606/61; 606/60; 606/53; 606/65
[58] Field of Search ........................ 606/61, 60, 53, 606/65

[56] References Cited

U.S. PATENT DOCUMENTS

| | | | |
|---|---|---|---|
| 5,176,679 | 1/1993 | Lin | 606/61 |
| 5,498,262 | 3/1996 | Bryan | 606/61 |
| 5,499,983 | 3/1996 | Hughes | 606/61 |
| 5,527,314 | 6/1996 | Brumfield et al. | 606/61 |
| 5,545,167 | 8/1996 | Lin | 606/61 |
| 5,662,653 | 9/1997 | Songer et al. | 606/61 |

*Primary Examiner*—Michael Buiz
*Assistant Examiner*—Tan-Uyen Thi Ho
*Attorney, Agent, or Firm*—Jacobson, Price, Holman & Stern, PLLC

[57] ABSTRACT

The bone-fixing devices which are designed to allow for a freer assembly of the parts which are mounted to maintain plurality of bones in a specified position relationship, and also call for only one or two parts to be tightened to assemble all parts into the whole system. A pedicle 10 to be implanted into a bone is connected by using a connector 20 with a shaft 30 that serves as a reference to position the bones. In order to ensure that the pedicle 10 is connected with the fixture 20, a shaft 12 is supported in a fork 21 formed at the end of the fixture 20, said short shaft 12 is fitted into a concave 11 formed at the head of the pedicle 10, and said short shaft 12 is fixed at the head of the pedicle with a retaining screw 13 so that the fixture 20 is mounted rotatably about the short shaft with reference to the pedicle 10.

4 Claims, 3 Drawing Sheets

BONE-FIXING DEVICES

BACKGROUND OF THE INVENTION

The present invention relates to bone-fixing devices which may be utilized to maintain plurality of bones in a specified positional relationship by installing a pedicle in each of the bones and employing a fixture to fix said pedicle to a reference shaft to position the bones.

A bone-fixing device of this type has various uses, such as disposing a reference shaft substantially in parallel with the spine and employing a fixture to fix a pedicle implanted in the vertebra thereof to said shaft. Although great care is exercised in implanting the pedicle in each vertebra, it is impossible to locate all the pedicles in the same direction, and in order to absorb the differences created, there is provided some range of adjustment at the junctions between the pedicle and the fixture, as well as between the fixture and the rod shaft.

An example of a bone-fixing device is disclosed by Japanese Patent Application laid-open No. 255739/95, in which a flange to be assembled in a pedicle and a member known as a lock pin are employed to achieve a construction in which some parts can be moved in two directions which perpendicularly intersect with each other. The distance between the pedicle and the shaft can be adjusted in the necessary range of adjustment by constructing a connecting means that can move to a suitable position along the bar of said connecting means. In the prior art device, according to that invention, it is necessary to carry out certain steps such as inserting the flange into the head of a screw to be threaded into the bone, inserting the lock pin into said head to fix the flange, putting the assembly into a connecting means and then inserting the connecting means into the bar to tighten it with a screw.

It is very troublesome, however, to require the foregoing complicated steps to assemble the above-mentioned parts into such a device and to adjust the position relationship between them. It is also difficult to reassemble these parts as necessary once they have temporarily been assembled. In addition, the device is designed so that the retaining screw is threaded into the bar in order to tighten the head of the bone screw which comes directly below said retaining screw, thus requiring the upper part of the bone screw to be open. This means that a wider incision range will be necessary to set the device, resulting in a prolonged operation time and curing period.

SUMMARY OF THE INVENTION

The bone-fixing devices of the present invention have been developed in view of the prior art described above, (including the drawbacks of prior art bone-fixing device,) and it is accordingly an object of the present invention to provide a greater degree of freedom with which to combine various parts into a bone-fixing device and greater ease with which to assemble them into the whole assembly by tightening one or two of them. This and other objects can be attained by the bone-fixing devices which comprise in such ways that in order to connect a pedicle 10 and a fixture 20, a short shaft 12 is supported in a fork 21 formed at the end of the fixture 20 and that the fixture 20 can be rotated around the short shaft with respect to the pedicle 10 by fitting said short shaft 12 into a concave 11 formed at the end of the pedicle 10 and securing the short shaft at the head of the pedicle by use of a retaining screw 13.

DETAILED DESCRIPTION OF PREFERRED EMBODIMENTS

The bone-fixing devices according to the present invention are so designed that plurality of pedicles 10, each being installed in a bone, is connected by means of a fixture 20 to a shaft 30 which serves as reference for positioning the bones.

Figure 1:
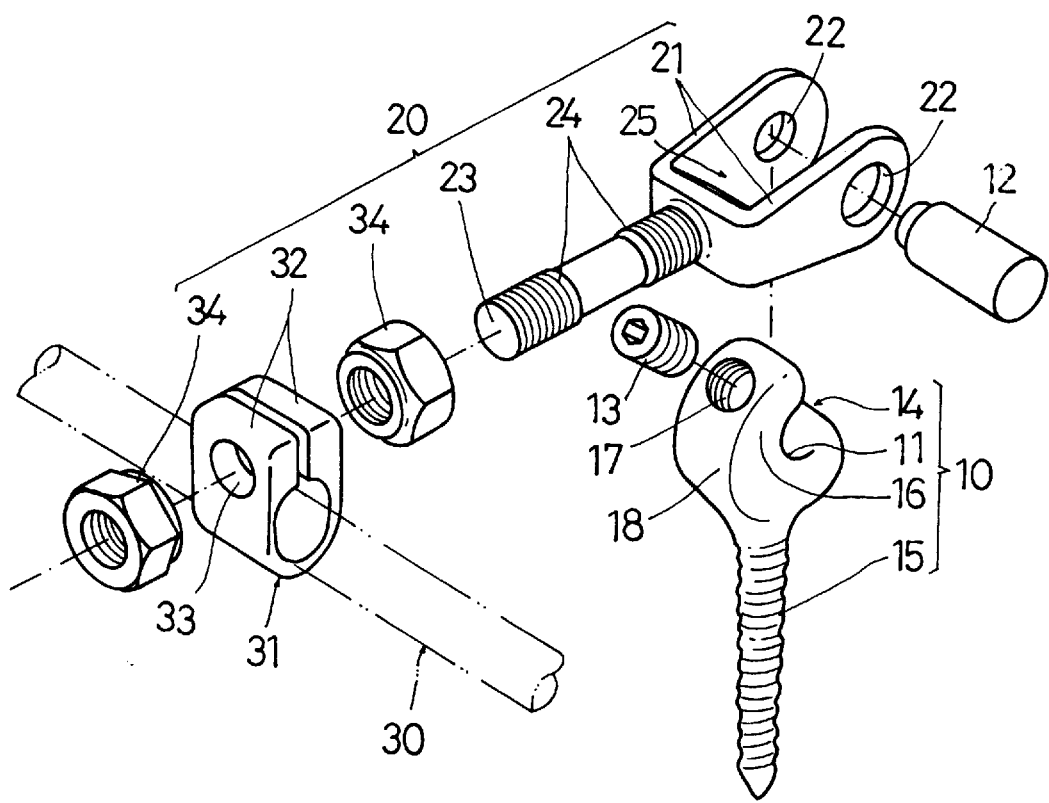
FIG. 1 is an exploded perspective view of bone-fixing devices according to the present invention.
Figure 2:
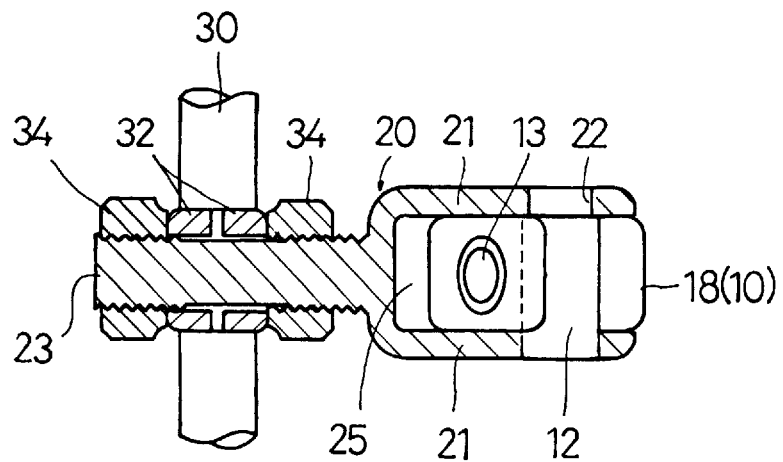
FIG. 2 is a horizontal sectional view of said device.
Figure 3:
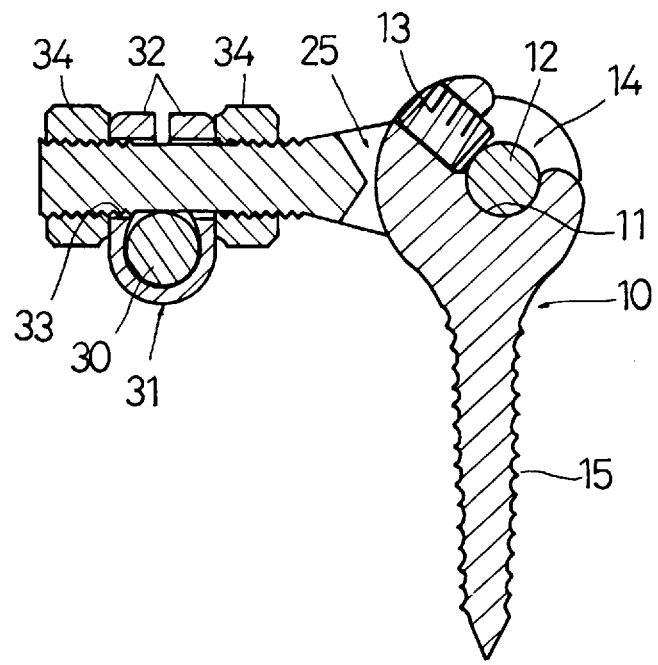
FIG. 3 is a vertical sectional view of said device.

The pedicle 10 comprises a threadable male screw thread which provides a means 15 for implanting said pedicle 10 into a bone, and a concave 11 in the head thereof for fitting a short shaft 12 on it. Said concave 11 has an inlet 14 for receiving said short shaft 12. If the inlet 14 is located behind the axis along which the pedicle 10 is threaded a wider incision range is required as in the case of the prior art bone-fixing devices, and if it is on the side of said direction, it is difficult to fit a short shaft into a pedicle. To solve these problems, the bone-fixing device according to the present invention is configured so that the inlet 14 is diagonally opposite the direction in which the pedicle 10 is threaded (FIG.3).

In order to connect the pedicle 10 and the fixture 20, the short shaft 12 is mounted in a fork 21 formed at the end of the fixture 20. The fork 21 is formed like double prongs adapted to support the short shaft 12 on both ends, said double prongs being provided with a supporting port 22. In the fork 21, there is provided between the double prongs a space 25 having a width sufficient to contain just the head 18 of the pedicle 10 to be fitted onto the short shaft 12. This arrangement eliminates the possibility that the short shaft 12 may be withdrawn from the fork 21 once the pedicle 10 is fixed onto the short shaft 12. In this preferred embodiment, one of the two ends of the short shaft 12 and the mating supporting port 22 adapted to receive said end of the short shaft are smaller in diameter than the other end of said shaft.

The short shaft 12 and the pedicle 10 are fixed by use of a retaining screw 13. The head 18 of the pedicle is formed like the letter "C" comprising an obliquely disposed inlet 14, as well as a long arm and a short arm. In the long arm 16, there is formed a female screw thread hole 17 which faces substantially toward the center of the concave 14, and which is adapted to receive the retaining screw 13. The short shaft 12 receives pressure from the retaining screw until it is completely fitted into the concave 11, and once it is fitted in, it is fixed in place so securely with the reaction force exerted by both long and short arms, that removal of the retaining screw will not result in the withdrawal of the head 18.

The fixture 20 comprises said fork portion 21 and a shaft portion 23. The shaft portion 23 faces the direction which perpendicularly intersects the axis of the short shaft 21 supported by the double-prong portion 21, and is provided with a connecting means between the fixture 20 and a reference shaft 30. Accordingly, this connecting means is also included as a component of the fixture 20.

The fixture has a U-shaped connector 31 to support the reference shaft 30. Both clamping ends 32, 32, of the connector 31 which are adapted to hold said shaft 30, there is formed a shaft hole 33 to support the shaft portion 23 of the fixture 20, and a nut 34 is threaded onto a male screw thread 24 formed in the shaft portion 23 to tighten the pieces 32, 32 together and secure the shaft 30. Instead of using two nuts 34, a female screw thread may be cut on one of the shaft holes 33 in the ends 32, 32.

The bone-fixing devices constructed according to the present invention ensure that the pedicle 10 and the shaft 23 of the fixture 20, and the shaft 23 and the shaft 30 as well, are established in a relationship in which their axes intersect perpendicularly to each other. The fixture 20 can be rotated around the short shaft 12 with respect to the pedicle 10, and can also be rotated around the shaft 23. The location of the shaft 30 with reference to the pedicle 10 can be adjusting the fixture 20 along the shaft 23 by employing the threads 23 or 24. The fixture 20 can be slided along the shaft 30, and the amount of the pedicle 10 being threaded into a bone can be adjusted.

Figure 4:
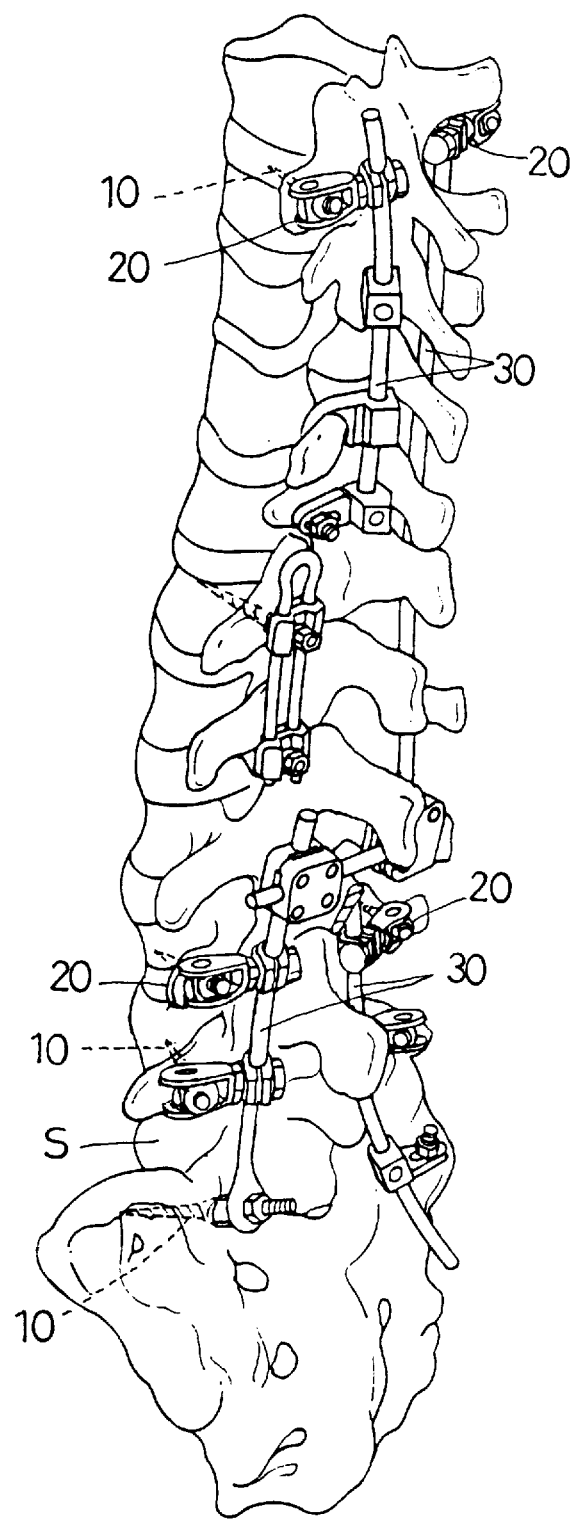
FIG. 4 illustrates application of the bone fixing devices shown in FIGS. 1–3.

The bone-fixing devices according to the present invention permit operators to implant the necessary number of pedicles 10 into the centrum of a vertebra S, fit a short shaft 12 into the concave 11 of each pedicle 10, shift the fixture 20 to each pedicle 10 on the shaft 30, use said range of adjustment to adjust the necessary parameters such as the distance and angle between the pedicle 10 and the fixture, and tighten the retaining screw 13 and the nuts 34. The direction in which the pedicle 10 is threaded may be varied as indicated in FIG. 4, but in the bone-fixing devices according to the present invention, the pedicle 10 is designed so that it can rotate around the shaft of the fixture which intersects perpendicularly thereto, and the fixture is movable axially to be adjusted on its own shaft and on the shaft 30. Thus the short shaft 12 is easy to fit into the concave 11, but once it is fitted in, it can no longer be easily withdrawn.

The bone-fixing devices according to the present invention are configured and operated in such a way that a greater degree of freedom is provided and the pedicle 10 and the shaft 30 can be connected by means of the connector 20. It also allows for a greater range of adjustment in the positioning of the shaft and the pedicle in a specified relationship, thereby enabling the operator to assemble these parts into the whole device quickly even through a narrow incision. This decreases the operation time and helps scars heal more quickly.

What is claimed is:

1. The bone-fixing devices for installing a pedicle into each bone by using a fixture, and for fixing said pedicle to a reference shaft in order to maintain plurality of bones in a specified relationship, said bone-fixing devices being so constructed that, in order to connect a pedicle 10 and a fixture 20, the fixture 20 is mounted rotatably to a short shaft with reference to the pedicle 10 by supporting the short shaft 12 with a fork 21 of the fixture 20, fixing it in a concave 11 formed at the head of the pedicle 10, then retaining it with a retaining screw 13 at the head of the pedicle 10.

2. The bone-fixing devices as claimed in claim 1, wherein said fixture 20 comprises a fork 21 and a shaft 23, said shaft facing the direction which intersects perpendicularly to the axis of the short shaft 12 supported by the fork 21, and having a male screw 24 thread at least at the end thereof.

3. The bone-fixing devices as claimed in claim 1, wherein a reference shaft 30 is supported by a substantially U-shaped connector 31, and the other end of the fixture 30 is supported by clamping pieces 32, 32 of the connector 31 which are adapted to hold the shaft 30, thereby establishing a perpendicularly intersecting relationship between the direction in which the fixture 20 is supported and the direction in which the shaft 30 is supported.

4. The bone-fixing devices as claimed in claim 1, wherein said concave 11 of the pedicle 10 is so configured that it has an inlet 14 disposed diagonally opposite to the direction in which the pedicle 10 is threaded, and that the short shaft 12 supported by the fork 21 is fitted from the inlet 14 into the concave 11 substantially in a parallel direction.

* * * * *